Figure 1:
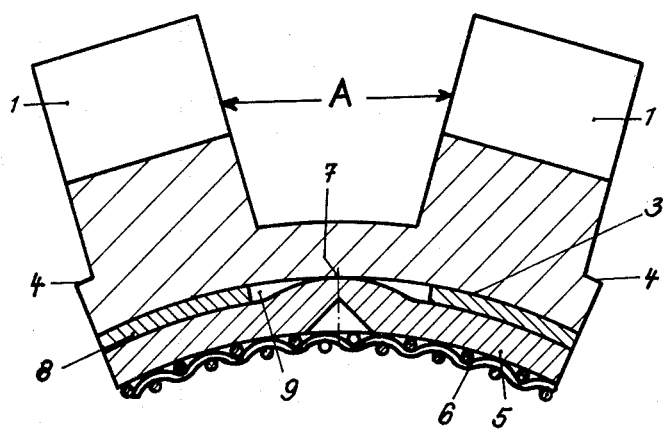

United States Patent [19]

Förster

[11] 4,256,455

[45] Mar. 17, 1981

[54] ORTHODONTIC BRACKET AND ORTHODONTIC APPLIANCE

[75] Inventor: Rolf Förster, Pforzheim, Fed. Rep. of Germany

[73] Assignee: Bernhard Förster GmbH, Pforzheim, Fed. Rep. of Germany

[21] Appl. No.: 42,855

[22] Filed: May 29, 1979

[30] Foreign Application Priority Data

Jun. 22, 1978 [DE] Fed. Rep. of Germany ....... 2818665

[51] Int. Cl.³ .............................................. A61C 7/00
[52] U.S. Cl. ............................................ 433/8; 433/9
[58] Field of Search ........................................ 433/8, 9

[56] References Cited

U.S. PATENT DOCUMENTS 4,068,379   1/1978   Miller et al. ............................ 433/9

*Primary Examiner*—Robert Peshock
*Attorney, Agent, or Firm*—Balogh, Osann, Kramer, Dvorak, Genova & Traub

[57] ABSTRACT

The bracket comprises a base which has an upwardly exposed portion and is free from resistance spot-weldable projections at its lower edges. Two anchoring means are spaced apart in the longitudinal direction of said base and rise therefrom on opposite sides of said central portion. Said anchoring means define a longitudinal groove. In the appliance, a mounting strap is connected to the underside of said base by a soldered joint under said anchoring means and by at least one spot weld.

8 Claims, 7 Drawing Figures

U.S. Patent   Mar. 17, 1981   4,256,455

ORTHODONTIC BRACKET AND ORTHODONTIC APPLIANCE

This invention relates to an orthodontic bracket, which is engageable by a tensioned wire used to correct a tooth and is adapted to be secured to a tooth to be corrected by the action of said tensioned wire or to a tooth to which said tensioned wire is to be anchored.

Specifically, the invention relates to such orthodontic brackets of that known type which comprises anchoring means consisting of two pairs of hooks, which are spaced apart in the longitudinal direction of the bracket and which define a longitudinal groove in which such tensioning wires can be guided and fixed.

The invention relates also to an orthodontic appliance comprising such bracket and a mounting strap for securing the bracket to a tooth.

Finally, the invention relates to a process of making such orthodontic appliance.

In known brackets of the type described hereinbefore, the hooks are carried by a base, which has flange lugs, which protrude beyond the hooks in the longitudinal direction of the bracket and are flush with the underside thereof. It is known to secure said flange lugs by a plurality of spot welds to a mounting strap, which is provided with a wire mesh layer on the side opposite to the bracket. Whereas it is desired in some cases to minimize the length of the brackets, said flange lugs add to such length.

It is an object of the invention to provide a bracket which combines small length and adequate strength.

It is another object of the invention to provide an orthodontic appliance in which the bracket is reliably secured to a mounting strap.

A further object of the invention is to provide a process which permits a short bracket to be reliably secured to a mounting strap.

To accomplish these and other objects, which will become apparent as the description proceeds, the invention provides an orthodontic bracket comprising a base portion and two pairs of hooks which extend upwardly from said base portion and are spaced apart in its longitudinal direction. Said base portion is free from spot-weldable projections at its lower edges.

The invention also provides an orthodontic appliance comprising said bracket and a mounting strap, which is provided with a wire mesh layer on the side opposite to the bracket. In that appliance, the base aperture of the bracket has a spot-weldable central portion between said hooks, a solder layer is disposed between and soldered to said mounting strap and said base and has an aperture adjacent to said central portion, and said mounting strap has an upwardly protruding arched portion which extends through said aperture and is spot-welded to said central portion.

This arrangement eliminates the need for spot-weldable projections at the lower edge of the base of the bracket so that the tooth area required for the mounting of the bracket can be greatly decreased. This permits of a greater latitude in the use of the bracket, as may be significant with teeth having surfaces which have a small radius of curvature or with closely spaced teeth.

Figure 2:
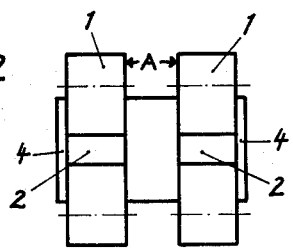
Figure 4:
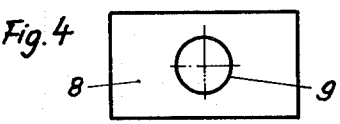
Figure 6:
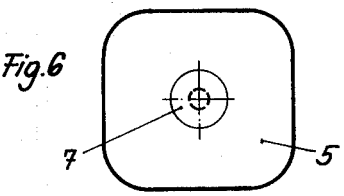

An embodiment of the orthodontic appliance according to the invention is shown by way of example on the accompanying drawings, in which FIG. 1 is a greatly enlarged sectional view showing the appliance;

FIGS. 2, 4, and 6 are top plan views showing components of the appliance, and

Figure 3:
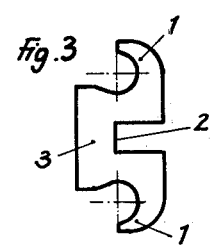
Figure 5:
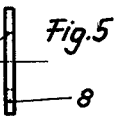
Figure 7:
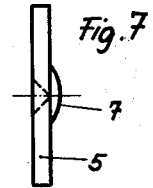

FIGS. 3, 5, and 7 are side elevations associated with FIGS. 2, 4, and 6, respectively.

As is apparent from the drawing, the orthodontic appliance comprises a bracket having two pairs of hooks 1, which are longitudinally spaced apart by the distance A and define a longitudinal groove 2, in which tooth-holding wires can be guided and fixed by known means. The bracket also comprises a base 3, which is free from spot-weldable projections at its lower edges.

In a central longitudinal sectional view, as shown in FIG. 1, the bracket has the shape of a truncated sector with two wings consisting of the pairs of hooks 1, which are spaced apart by the distance A. At its ends, the base of the bracket may protrude in its longitudinal direction beyond the hooks 1 but said protruding portions 4 are so thick that they cannot be spotwelded.

It is also apparent from FIGS. 1 to 7 that the bracket is secured to a mounting strip 5, which on the side opposite to the bracket has a wire mesh layer 6, which is adapted to be secured to a tooth or a tooth-connecting strap. The mounting strap has an arched portion 7, which is spot-welded to the central portion of the bracket between the hooks. That central portion is sufficiently thin so that it can be spot-welded. Around said spot weld, and particularly under the hooks 1, the mounting strap is bonded to the base 3 by a soldered joint. That soldered joint has been made with the aid of a solder sheet 8, which has been placed between the mounting strap 5 and the base 3. Under the central portion of the base, the solder sheet has an aperture 9 through which the upwardly protruding arcuate portion 7 extends to contact the base 3. Very small orthodontic appliances can be made in this way.

In an alternative mode of making the bracket assembly, a soldering sheet is placed between the mounting strap and the bracket and is used to join said two parts by a soldered joint, and the mounting strap is additionally spot-welded to the base under the hooks by means of a laser.

What is claimed is:

1. An orthodontic bracket assembly comprising
   a bracket having a base which has an upwardly exposed central portion and which is free from resistance spot-weldable projections at its lower edges, and two anchoring means which are spaced apart in the longitudinal direction of said base and rise therefrom on opposite sides of said central portion and define a longitudinal groove, and
   a mounting strap which is connected to the underside of said base by a soldered joint under said anchoring means,
   said soldered joint having an aperature under said central portion and said mounting strap having an upwardly protruding arched portion which extends through said aperture and is joined to said central portion by a spot weld so as to reliably secure said mounting strap to said bracket.

2. An orthodontic bracket as set forth in claim 1, in which each of said anchoring means comprises a pair of hooks.

3. An orthodontic bracket as set forth in claim 1, in which said central portion is sufficiently thin for being resistance spot-welded.

4. An orthodontic bracket as set forth in claim 1, in which said bracket in a central longitudinal sectional view has the shape of a truncated sector having two rising wings constitued by said anchoring means.

5. An orthodontic bracket as set forth in claim 4, in which said bracket has end portions which protrude in longitudinal direction beyond said anchoring means and are too thick to be resistance spot-welded.

6. An orthodontic bracket assembly as set forth in claim 1, in which said mounting strap is joined to said base under said anchoring means by laser spot welds.

7. An orthodontic bracket assembly as set forth in claim 1, in which said mounting strap is provided with a wire mesh layer on the side opposite to said base.

* * * * *